(12) United States Patent
Abbasi

(10) Patent No.: US 11,504,165 B1
(45) Date of Patent: Nov. 22, 2022

(54) ASYMMETRIC CLAMP WITH ULTRASONIC TISSUE REMOVAL CAPABILITY

(71) Applicant: Advance Research System, LLC, Edina, MN (US)

(72) Inventor: Hamid Abbasi, Edina, MN (US)

(73) Assignee: Advance Research System, LLC, Edina, MN (US)

( * ) Notice: Subject to any disclaimer, the term of this patent is extended or adjusted under 35 U.S.C. 154(b) by 384 days.

(21) Appl. No.: 16/599,802

(22) Filed: Oct. 11, 2019

Related U.S. Application Data

(60) Provisional application No. 62/748,817, filed on Oct. 22, 2018, provisional application No. 62/773,629, filed on Nov. 30, 2018.

(51) Int. Cl.
*A61B 17/16* (2006.01)
*A61B 17/32* (2006.01)
*A61B 17/70* (2006.01)

(52) U.S. Cl.
CPC ...... *A61B 17/7049* (2013.01); *A61B 17/1606* (2013.01); *A61B 17/1671* (2013.01); *A61B 17/320092* (2013.01); *A61B 17/7019* (2013.01); *A61B 17/7043* (2013.01); *A61B 17/7076* (2013.01)

(58) Field of Classification Search
CPC ............ A61B 17/7043; A61B 17/7047; A61B 17/7049; A61B 17/7076
See application file for complete search history.

(56) References Cited

U.S. PATENT DOCUMENTS

| | | | |
|---|---|---|---|
| 5,236,358 A | 8/1993 | Sieffert | |
| 5,322,055 A | 6/1994 | Davison et al. | |
| 5,342,380 A | 8/1994 | Hood | |
| 5,437,669 A * | 8/1995 | Yuan ................... | A61B 17/7047 606/264 |
| 6,190,392 B1 | 2/2001 | Vandewalle et al. | |
| 6,283,981 B1 | 9/2001 | Beaupre | |
| 6,602,253 B2 * | 8/2003 | Richelsoph ........ | A61B 17/7052 606/252 |
| 6,866,664 B2 * | 3/2005 | Schär ................. | A61B 17/7052 606/252 |
| 6,976,969 B2 | 12/2005 | Messerly | |
| 7,717,938 B2 * | 5/2010 | Kim ................... | A61B 17/7083 606/250 |
| 8,002,782 B2 | 8/2011 | Witt et al. | |

(Continued)

*Primary Examiner* — Nicholas W Woodall
(74) *Attorney, Agent, or Firm* — Christensen, Fonder, Dardi & Herbert PLLC; Stuart J. Olstad

(57) ABSTRACT

An ultrasonically assisted clamping system and method for extending a spinal support rod system to additional vertebrae of the spine. A clamp assembly and a receptacle assembly securely couple an additional extension rod to an existing spinal support rod. Various embodiments further include an ultrasonic assist for cutting through tissue that may be present in the vicinity of the existing spinal support rods. In some embodiments, the clamp assembly is configured to augment the ultrasonic aspect of the system. The system cuts through and locally removes tissue from and proximate to the spinal support rods where the clamp assembly is to be mounted, without the need for a separate surgical procedure for removing the tissue prior to implantation, thereby providing a secure clamping of the newly implanted extension rod to the existing base spinal support rod.

13 Claims, 15 Drawing Sheets

(56) References Cited

U.S. PATENT DOCUMENTS

| | | |
|---|---|---|
| 8,353,912 B2 | 1/2013 | Darian et al. |
| 8,419,640 B1 | 4/2013 | Saha |
| 9,241,730 B2 | 1/2016 | Babaev |
| 9,408,622 B2 | 8/2016 | Stulen et al. |
| 9,439,670 B2 | 9/2016 | Witt et al. |
| 9,486,234 B2 | 11/2016 | Babaev |
| 10,039,573 B2* | 8/2018 | Khajavi ............ A61B 17/00234 |
| 10,321,939 B2* | 6/2019 | Lee .................... A61B 17/8645 |
| 10,624,678 B2* | 4/2020 | Lasswell ............ A61B 17/7076 |
| 2006/0100548 A1 | 5/2006 | Ferguson |
| 2013/0165976 A1* | 6/2013 | Gunn ................. A61B 17/7052 |
| | | 606/253 |
| 2019/0269469 A1* | 9/2019 | Bush, Jr. ................ A61B 34/76 |

* cited by examiner

```
                                                          260
┌─────────────────────────────────────────┐              ↙
│ providing a rod receptacle and a clamping│
│ assembly, and providing operating instructions│
│ on a tangible, non-transitory medium    │
│                                     262 │
└─────────────────────────────────────────┘

┌─────────────────────────────────────────┐  ⎫
│ connecting an ultrasonic generator to a coupling│
│ of the clamping assembly                │
│                                     264 │
└─────────────────────────────────────────┘

┌─────────────────────────────────────────┐
│ energizing the ultrasonic generator to  │
│ ultrasonically vibrate the clamping assembly│
│                                     266 │
└─────────────────────────────────────────┘

┌─────────────────────────────────────────┐
│ cutting through tissue that is on and in the│
│ vicinity of the base spinal support rod with the│
│ clamping assembly                       │
│                                     268 │
└─────────────────────────────────────────┘           Operating
                                                       Instructions
┌─────────────────────────────────────────┐              258
│ disconnecting the ultrasonic generator from the│
│ clamping assembly                   270 │
└─────────────────────────────────────────┘

┌─────────────────────────────────────────┐
│ coupling the rod receptacle to the coupling of│
│ the clamping assembly               272 │
└─────────────────────────────────────────┘

┌─────────────────────────────────────────┐
│ engaging an engagement surface of a first jaw│
│ of the clamping assembly with the base spinal│
│ support rod                         274 │
└─────────────────────────────────────────┘

┌─────────────────────────────────────────┐
│ translating a second jaw of the clamping│
│ assembly onto the base spinal support rod  276│
└─────────────────────────────────────────┘

┌─────────────────────────────────────────┐
│ affixing the clamping assembly to a base spinal│
│ support rod                         278 │  ⎭
└─────────────────────────────────────────┘

FIG. 16
```

ASYMMETRIC CLAMP WITH ULTRASONIC TISSUE REMOVAL CAPABILITY

RELATED APPLICATIONS

This application claims the benefit of U.S. Provisional Application No. 62/748,817, filed Oct. 22, 2018, and of U.S. Provisional Application No. 62/773,629, filed Nov. 30, 2018, the disclosures of which are hereby incorporated by reference in their entirety.

FIELD OF THE DISCLOSURE

The present disclosure relates to spinal support systems and more particularly to a spinal support system that is extensible.

BACKGROUND OF THE DISCLOSURE

Implementation of various spinal surgical techniques often require the use of spinal support rods that are anchored to the vertebrae through the use of pedicle screws to provide stabilization of the spine during healing or correction. Examples include maintaining adjacent vertebrae stationary so that bone growth tissue can bridge the vertebrae in a spinal fusion process. Another example is the use of spinal support rods to apply a coercive force to the spine for corrective purposes (e.g., correction of scoliosis).

In some cases, surgery is later required to treat other vertebrae of the same patient. One technique is to extend additional spinal support rods from the existing, already-implanted spinal support rods. The additional rods are affixed to the existing rods using clamps that grip the existing rods and provide a housing from which the additional rod can be extended. Such an extension system is found, for example, at U.S Patent Application Publication No. 2016/0242817 ('817 Publication) to Abbasi entitled "Spinal Rod Support Structure with Clamp," owned by the owner of the current application, the contents of which are incorporated by reference herein except for patent claims and express definitions contained therein. The present application identifies shortcomings in the art of spinal rod extension systems and provides improvements to remedy such shortcomings.

SUMMARY OF THE DISCLOSURE

Various embodiments of the present application disclose an ultrasonically assisted clamping system for extending a spinal support rod system to additional vertebrae of the spine. Over time, after implantation of spinal support rods, tissue can grow around and adhere to the existing rods. The presence of the tissue can interfere with the clamping operation of the extension system and compromise or limit the magnitude of the coercive force that can be applied to the spine.

As with the '817 Publication, the disclosed system utilizes a clamp assembly and a receptacle assembly to securely couple an additional extension rod to an existing spinal support rod. Various embodiments disclosed herein further include an ultrasonic assist for cutting through tissue that may be present in the vicinity of the existing spinal support rods. In some embodiments, the clamp assembly is configured to augment the ultrasonic aspect of the system. The system cuts through and locally removes tissue from and proximate to the spinal support rods, without the need for the trauma of removing the tissue in an additional step prior to implantation, to provide a secure clamping of the newly implanted extension rod to the existing base spinal support rod. That is, the clamp assembly is configured for alternative attachment of both an ultrasonic generation source and an extension receptacle for securing the additional spinal support rod. In some embodiments, an asymmetric aspect of the clamp assembly enables secure clamping to the existing spinal support rod.

Structurally, various embodiments of the disclosure include an ultrasonically assisted clamping system, comprising a clamp assembly including a first clamping jaw and a second clamping jaw configured for mounting to a base spinal support rod. In some embodiments, the clamp assembly is configured for selective coupling to an ultrasonic generator when the ultrasonically assisted clamping system is in a vibration configuration, and the clamp assembly is configured for securing the clamp assembly to a base spinal support rod when the ultrasonically assisted clamping system is in an implanted configuration. The first clamping jaw and the second clamping jaw may extend in an axial direction parallel to a central axis of the clamp assembly, the first clamping jaw defining a first axial length in the axial direction, the second clamping jaw defining a second axial length in the axial direction, the first axial length being greater than the second axial length. In some embodiments, the clamp assembly includes a housing, the first clamping jaw being integral with the housing, the second clamping jaw being disposed in the housing and translatable parallel to the central axis. In some embodiments, a first engagement surface of the first clamping jaw defines a first distal tangential extremity, and a second engagement surface of the second clamping jaw defines a second distal tangential extremity. The first distal tangential extremity and the second distal tangential extremity may define an angular gap therebetween when the clamp assembly is in the implanted configuration, the angular gap being defined from a midpoint axis defined by the first clamping jaw and the second clamping jaw. In some embodiments, the angular gap is in a range of 60 degrees to 165 degrees inclusive. The central axis of the clamp assembly may pass through the angular gap when the clamp assembly is in the implanted configuration. In some embodiments, when affixed to a base spinal support rod in the implanted configuration, a distal edge of the first clamping jaw and a distal edge of the second clamping jaw of the ultrasonically assisted clamping system do not extend distal to the base spinal support rod. In some embodiments, at least one of the first clamping jaw and the second clamping jaw includes a plurality of teeth at a distal end thereof. The teeth may include a matrix of pyramidal projections. Also, each pyramidal projection may define a base dimension and a height dimension, each of the base dimension and the height dimension being within a range of 50 micrometers to 300 micrometers inclusive.

In various embodiments of the disclosure, the ultrasonically assisted clamping system includes a housing, the first clamping jaw being integral with the housing. An extension receptacle assembly may coupled to a proximal end of the clamp assembly when the ultrasonically assisted clamping system is in the implanted configuration. The clamp assembly may include a coupler for selective connection of both of the extension receptacle assembly and the ultrasonic generator. In some embodiments, the coupler is a threaded coupling. The ultrasonically assisted clamping system may include an ultrasonic generator.

In various embodiments of the disclosure, a method for mounting an extension receptacle assembly to an existing base spinal support rod of a spinal support system comprises providing a rod receptacle and a clamp assembly, and providing operating instructions on a tangible, non-transitory medium, the operating instructions including: connecting an ultrasonic generator to a coupler of the clamp assembly; energizing the ultrasonic generator to ultrasonically vibrate the clamp assembly; disconnecting the ultrasonic generator from the clamp assembly; mounting the rod receptacle to the coupler of the clamp assembly; and with the rod receptacle mounted to the coupler of the clamp assembly, affixing the clamp assembly to a base spinal support rod. In some embodiments of the disclosure, the operating instructions include engaging an engagement surface of a first jaw of the clamp assembly with the base spinal support rod, and, with the engagement surface of the first jaw of the clamp assembly engaged with the base spinal support rod, translating a second jaw of the clamp assembly onto the base spinal support rod. The operating instructions may also include cutting through tissue that is on and in the vicinity of the base spinal support rod with the clamp assembly after the step of energizing the ultrasonic generator to ultrasonically vibrate the clamp assembly. In some embodiments, the instructions include performing the step of cutting through tissue that is on and in the vicinity of the base spinal support rod with teeth formed at a distal end of the clamp assembly.

BRIEF DESCRIPTION OF THE DRAWINGS

FIG. 7 is an enlarged, partial perspective view of a plurality of teeth disposed at a distal end of a clamping jaw according to an embodiment of the disclosure;

FIG. 16 is a flow diagram of a method of using the ultrasonically assisted clamping system of FIG. 1 according to an embodiment of the disclosure.

DETAILED DESCRIPTION OF THE FIGURES

Figure 1:
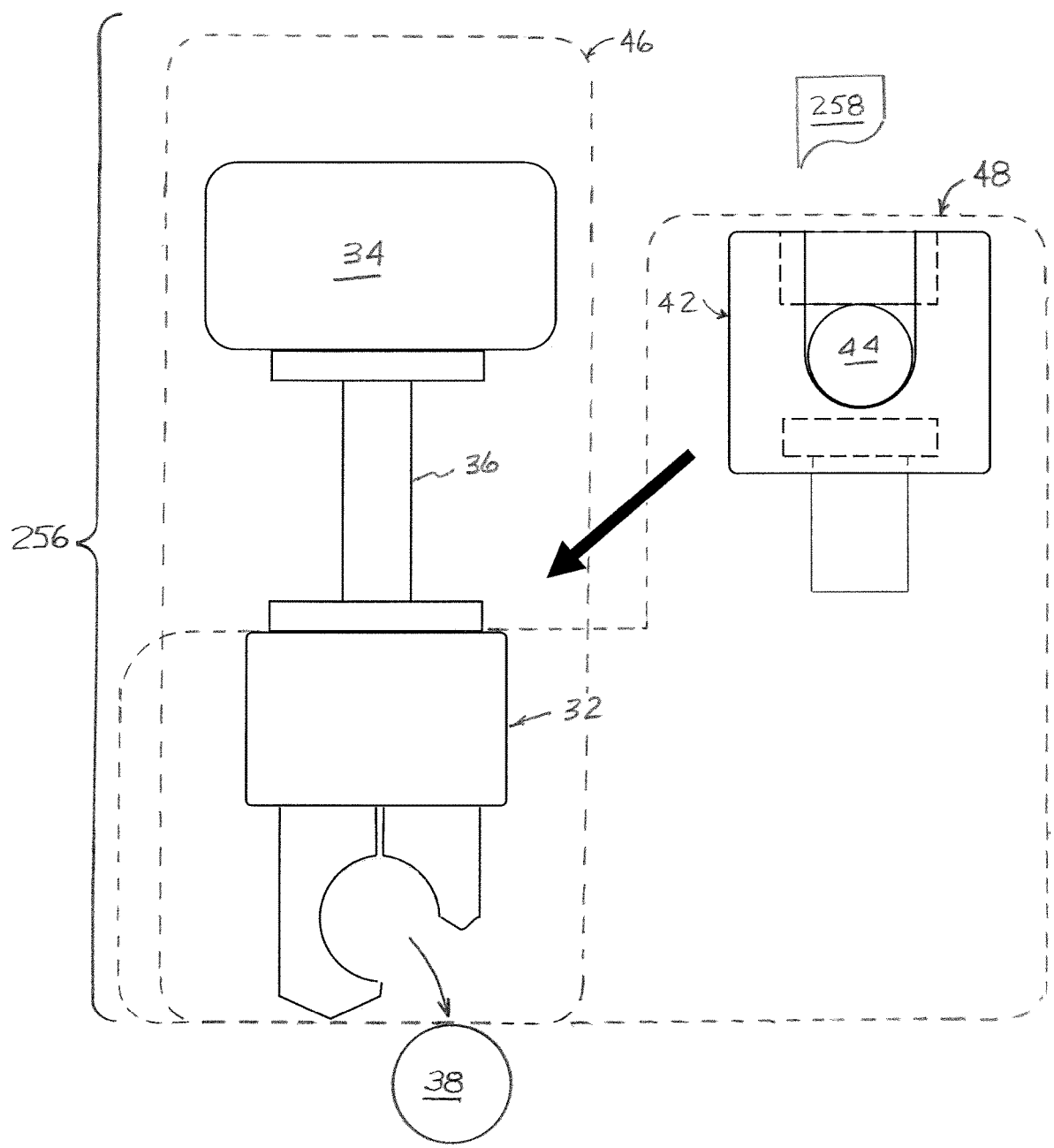
FIG. 1 is a schematic of an ultrasonically assisted clamping system according to an embodiment of the disclosure.
Figure 2:
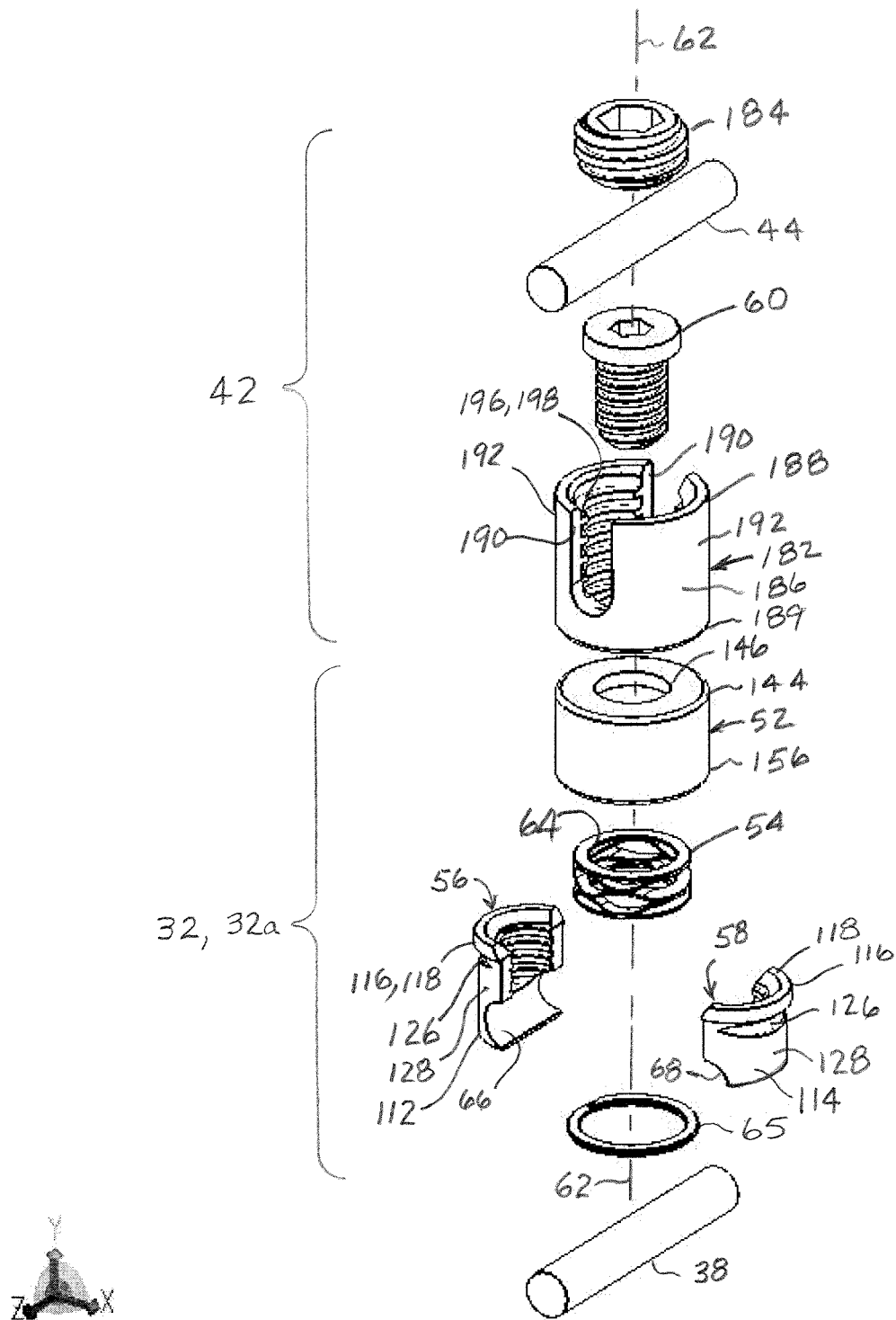
FIG. 2 is an exploded, upper perspective view of a clamp assembly having rotating jaws in combination with a receptacle assembly according to an embodiment of the disclosure.
Figure 3:
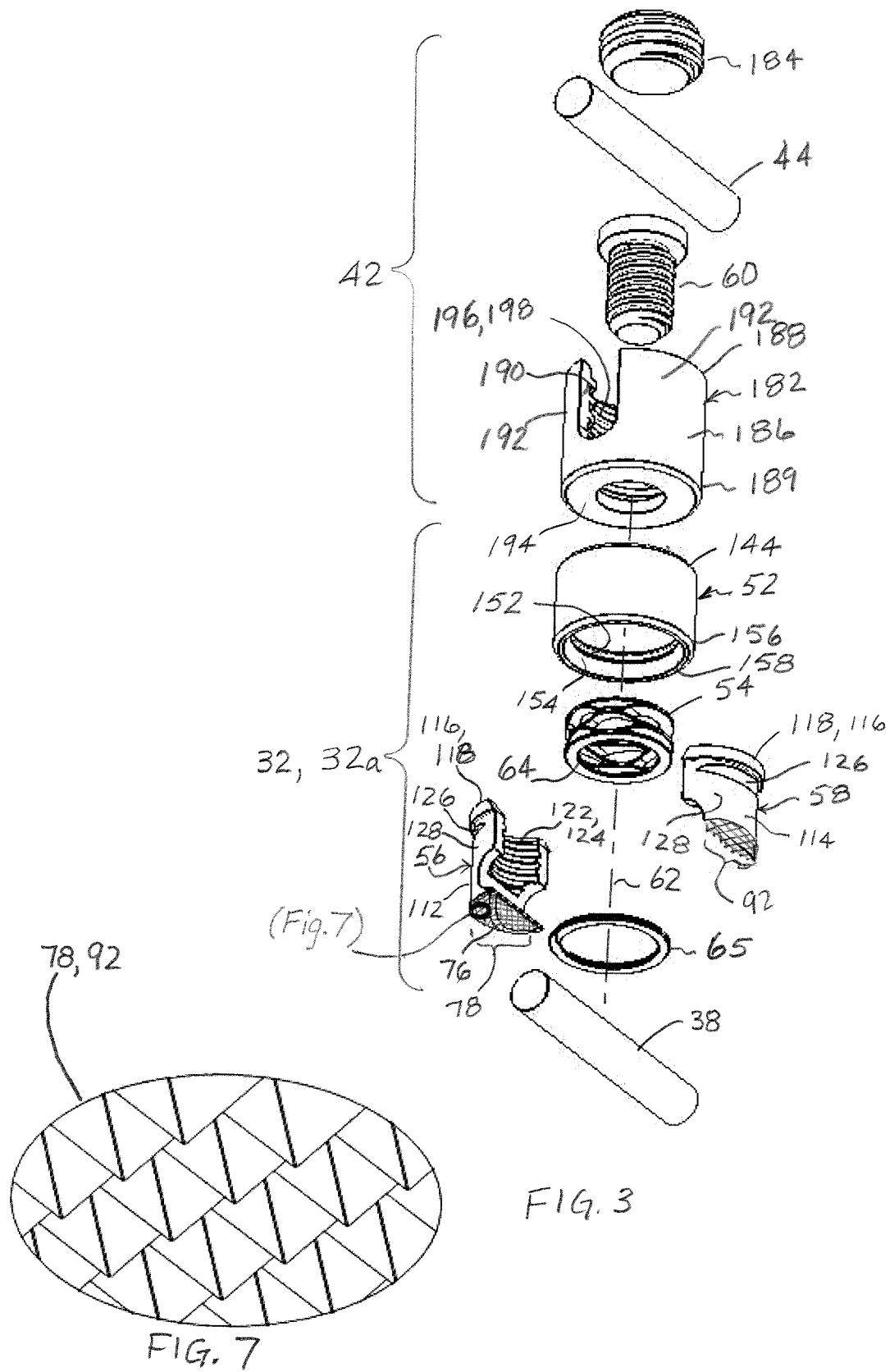
FIG. 3 is an exploded, lower perspective view of the clamp assembly and receptacle assembly of FIG. 2 according to an embodiment of the disclosure.

Referring to FIG. 1, a schematic of an ultrasonically assisted clamping system 30 is depicted according to an embodiment of the disclosure. The ultrasonically assisted clamping system 30 includes a clamp assembly 32 and an ultrasonic generator 34 that are coupled together with an ultrasonic transmission line 36. In some embodiments, upon implantation of the clamp assembly 32 onto an existing or base spinal support rod 38, the ultrasonic transmission line 36 is detached from the clamp assembly 32 and an extension receptacle assembly 42 coupled to the clamp assembly 32. An extension spinal support rod 44 is secured to the extension receptacle assembly 38.

In some embodiments, the ultrasonically assisted clamping system 30 is configurable in two modes or configurations: a vibration configuration 46 and a clamping or implanted configuration 48. In the vibration configuration, the clamp assembly 32 is used as a vibration-assisted cutter that cuts through tissue that may, over time, have grown adjacent the base spinal support rod 38, enabling insertion of the clamp assembly 32 through the tissue. In the implanted configuration 48, the clamp assembly 32 is secured to the base spinal support rod 38 and fitted with the extension receptacle assembly 42 for implantation of the extension spinal support rod 44.

Herein, a plurality of clamp assemblies 32 are presented. The clamp assemblies are referred to generically or collectively by reference character 32, and specifically or individually by reference character 32 followed by a letter suffix (e.g., "clamp assembly 32*a*").

Referring to FIGS. 2 through 6, a clamp assembly 32*a* is depicted according to an embodiment of the disclosure. The clamp assembly 32*a* includes a housing 52 that houses a spring 54 and two clamping jaws 56 and 58 that are opposed about a central axis 62. The spring 54 may be a wave spring (depicted), a wave washer, a standard coil spring, or any spring available to the artisan. In some embodiments, the spring 54 defines a central passage 64 for passage of a fastener 60 therethrough. The spring 54 and jaws 56, 58 are retained within the housing 52 with a lock ring 65.

Figure 5:
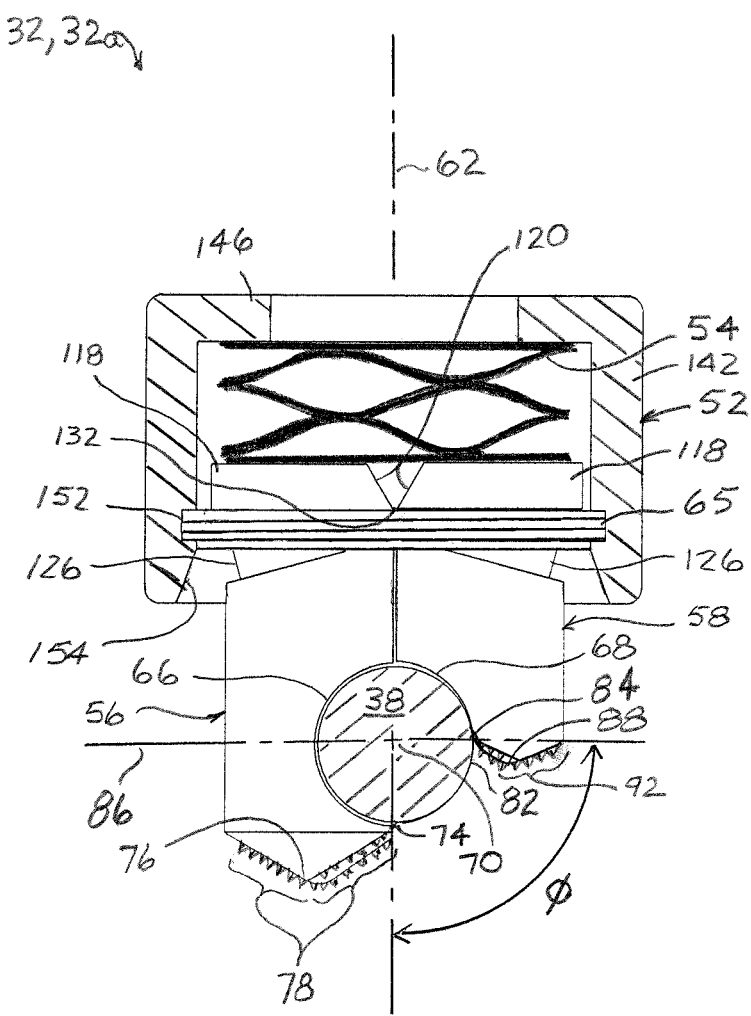
FIG. 5 is a partial sectional side view of the clamp assembly of FIG. 4 with the base spinal support rod captured by the clamp assembly according to an embodiment of the disclosure.

In the depicted embodiment, the clamping jaws 56 and 58 are asymmetric, with clamping jaw 56 being longer than clamping jaw 58 along the central axis 62. Each of the clamping jaws 56 and 58 include an engagement surface 66 and 68, respectively, for engagement of the base spinal support rod 38. The engagement surfaces 66 and 68 cooperate to define a midpoint axis 70 about which the base spinal support rod 38 is substantially centered when captured and secured by the clamping jaws 56 and 58. In the depicted embodiment, the midpoint axis 70 is orthogonal to the central axis 62 and the lateral axis 86. In some embodiments, the engagement surface 66 of the longer clamping jaw 56 extends around to a distal portion 72 of the base spinal support rod 38. In the depicted embodiment of the clamp assembly 32a, a distal tangential extremity 74 of the engagement surface 66 of the longer clamping jaw 56 reaches the central axis 62 when in the clamped configuration (FIG. 5). Embodiments are also contemplated where the distal tangential extremity 74 does not reach the central axis 62 (e.g., clamp assemblies 32b and 32c described below), or, alternatively, reaches beyond the central axis 62. The longer clamping jaw 56 includes a distal edge or ridge structure 76 that may include a plurality of teeth 78.

The engagement surface 68 of the shorter clamping jaw 58 extends around to a mid-portion 82 of the base spinal support rod 38. In the depicted embodiment, a distal tangential extremity 84 of the engagement surface 68 of the shorter clamping jaw 58 reaches a lateral axis 86 that passes through the midpoint axis 70 of the clamping jaws 56 and 58 and is perpendicular to the central axis 62. Embodiments are also contemplated where the distal tangential extremity 84 does not reach the lateral axis 86, or, alternatively, reaches beyond the lateral axis 86. The shorter clamping jaw 58 includes a distal edge or ridge structure 88 that may also include a plurality of teeth 92.

In operation, the ultrasonic generator 34 and transmission line 36 are coupled to the clamp assembly 32 in the vibration configuration 46 of the ultrasonically assisted clamping system 30 as depicted in FIG. 1. The ultrasonic generator 34 is energized so that the clamp assembly 32 is pulsed with ultrasonic vibration. The clamp assembly 32 may be used to cut through tissue in the vicinity of the base spinal support rod 38 with the teeth 78, 92 and inserted through the tissue. In this way, only the tissue that needs to be separated and removed from the base spinal support rod 38 and vicinity is affected, while providing a stable coupling between the clamp assembly 32 and the base spinal support rod 38.

Figure 4:
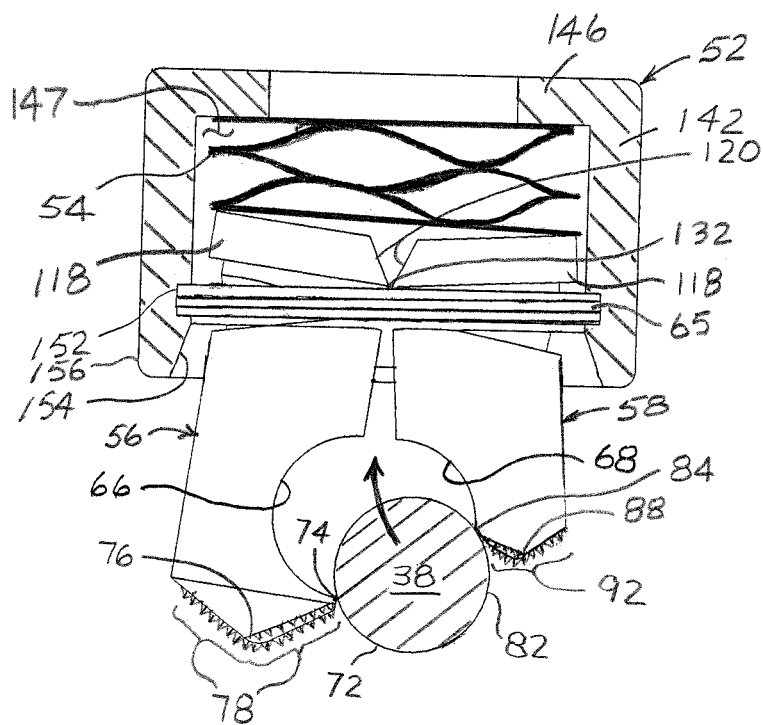
FIG. 4 is a partial sectional side view of a clamp assembly being slid over a base spinal support rod according to an embodiment of the disclosure.

To implant the clamp assembly 32a, the clamp assembly 32a is slid over the base spinal support rod 38, with the clamping jaws 56 and 58 being separated as they pass over the base spinal support rod 38 (FIG. 4). The clamping jaws 56 and 58 pass over the base spinal support rod 38 and are drawn together to capture the base spinal support rod 38 (FIG. 5). The clamp assembly 32a, including the engagement surfaces 66 and 68, distal tangential extremities 74 and 84, distal edges 76 and 88, and pluralities of teeth 78 and 92, are pulsed with the ultrasonic energy that helps cut through built up tissue that is on and in the vicinity of the base spinal support rod 38. In some embodiments, once the engagement surface 66 of the longer clamping jaw 56 is substantially in place on the base spinal support rod 38, the ultrasonically assisted clamping system 30 is configured in the implanted configuration 48 for implantation of the clamp assembly 32 and extension spinal support rod 44.

The clamping jaws 56 and 58 include body portions 112 and 114, respectively, each having a proximal end 116. In some embodiments, each body portion 112, 114 includes a flange portion 118 at the proximal end 116 and may further include a semicircular interior surface 122 about the central axis 62. The flange portions 118 may include chamfers 120 at the interface of the clamping portions 56 and 58. In some embodiments, the semicircular interior surface 122 included threads 124. The threads 124 of the body portions 112 and 114 cooperate to define a threaded passage for threaded engagement with the fastener 60. The body portions 112 and 114 may each define a tangential relief slot 126 on an exterior surface 128 thereof that extends tangentially and at least partially about the central axis 62.

In the depicted embodiment, the housing 52 includes a side wall 142 having a proximal end 144 with a flange portion 146 that extends radially inward from the side wall 142. The housing 52 may also define an interior chamber 147 that includes an interior surface 148 defining a groove 152 that surrounds the central axis 62. In some embodiments, a distal end 156 of the housing 52 may include an inclined surface 154 that extends radially outward and away from the proximal end 144 to define a flared inlet 158 at the distal end 156 of the housing 52.

In assembly, the spring 54 is inserted into the housing 52 from the distal end 156 and registered against the flange portion 146 of the housing 52. The clamping jaws 56 and 58 are inserted into the distal end 156, putting the spring 54 in compression. In the depicted embodiment, the clamping jaws 56 and 58 are brought together in a clamped configuration (FIG. 5, sans the base spinal support rod 38) and the lock ring 65 slid over the body portions 112 and 114 toward the flange portions 118. At the distal end 156, the lock ring 65 may be contracted radially inward to pass through the flared surface 154 and snap into place in the groove 152. Accordingly, for the fully assembled depicted embodiment, the flange portions 118 of the clamping jaws 56 and 58 register against the lock ring 65, which retains the clamping jaws 56 and 58 and the spring 54 within the housing 52.

Functionally, the spring 54 biases the clamping jaws 56 and 58 toward the clamped configuration (i.e., toward each other). When the clamping jaws 56 and 58 are separated to pass over the base spinal support rod 38, the clamping jaws 56 and 58 pivotally rotate about a pivot line 132 at the base of the chamfers 120, causing the flange portions 118 to rotate away from the lock ring 65. This rotation places the spring 54 in compression or increased compression (FIG. 4). The spring-loaded arrangement of FIGS. 4 and 5 enable the clamping jaws 56 and 58 to be passively separated by the base spinal support rod 38 as the clamp assembly 32a is slid onto the base spinal support rod 38. As the distal tangential extremities 74 and 84 of the clamping jaws 56 and 58 pass over the base spinal support rod 38, the bias force exerted by the spring 54 force the clamping jaws 56 and 58 toward each other so that the engagement surfaces 66 and 68 engage the base spinal support rod 38. The tangential relief slots 126 serve two purposes: (1) to enable the lock ring 65 to be contracted radially inward during assembly for engagement in the groove 152, and (2) to enable the clamping jaws 56 and 58 to rotate outward (i.e., away from the central axis 62) while pivoting about their respective flange portions 118 at line 132. In the clamped configuration of FIG. 5, the clamping jaws 56 and 58 also cooperate to define the threaded passage for threaded engagement with the fastener 60.

Figure 6:
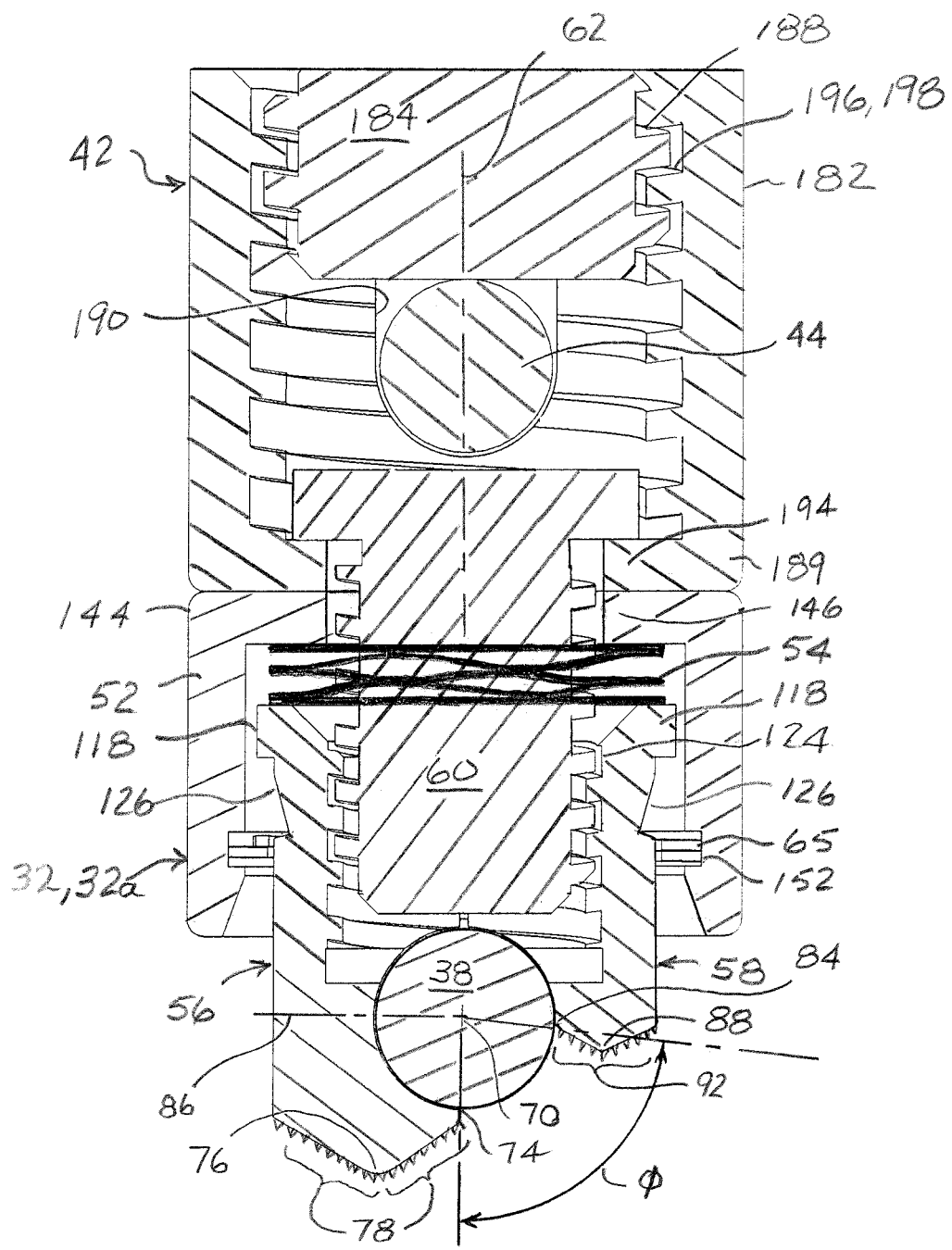
FIG. 6 is a sectional view of the clamp assembly and receptacle assembly of FIG. 2 fully assembled and secured to the base spinal support rod and an extension spinal support rod according to an embodiment of the disclosure.
Figure 8:
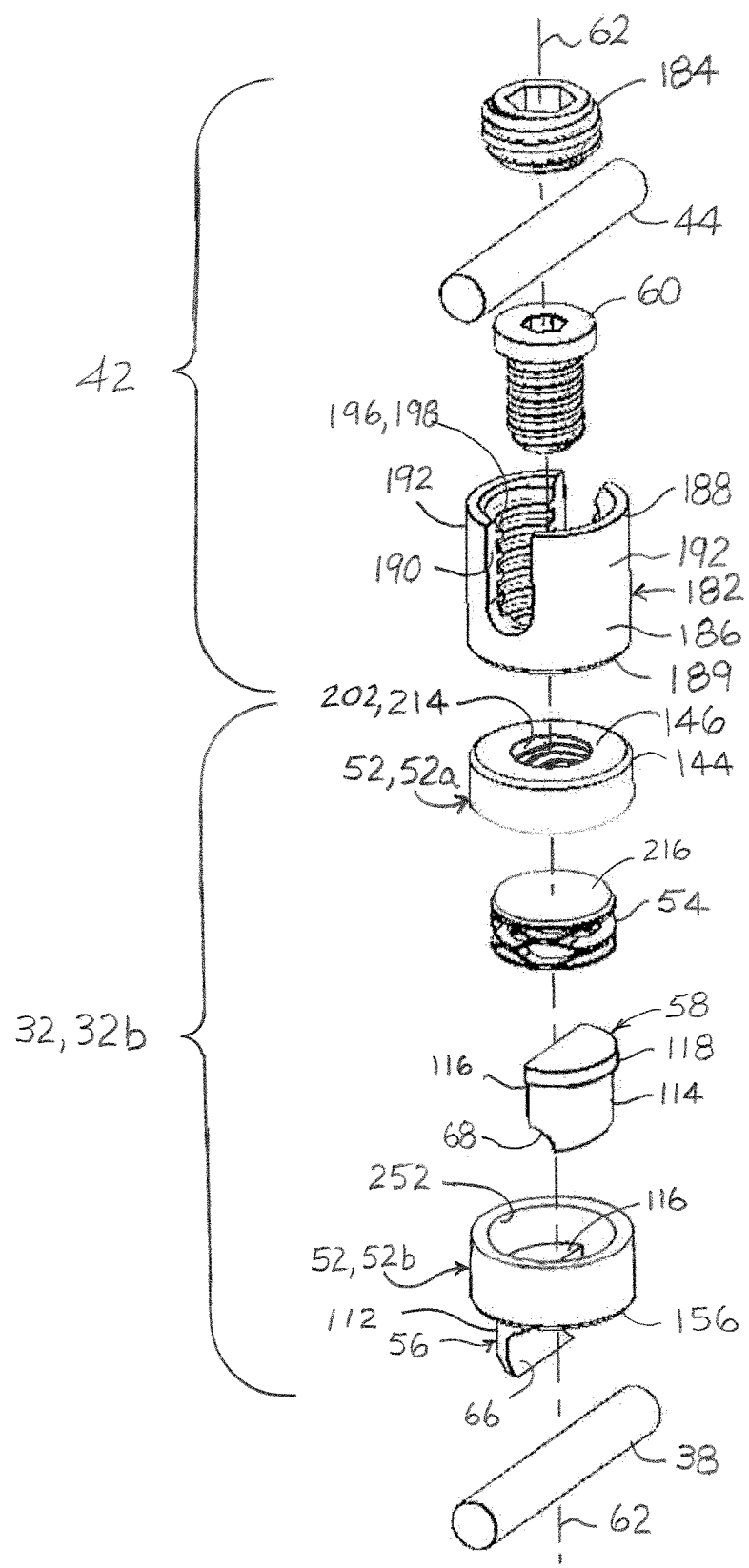
FIG. 8 is an exploded, upper perspective view of a clamp assembly having a fixed jaw and a spring loaded translatable jaw in combination with a receptacle assembly according to an embodiment of the disclosure.
Figure 9:
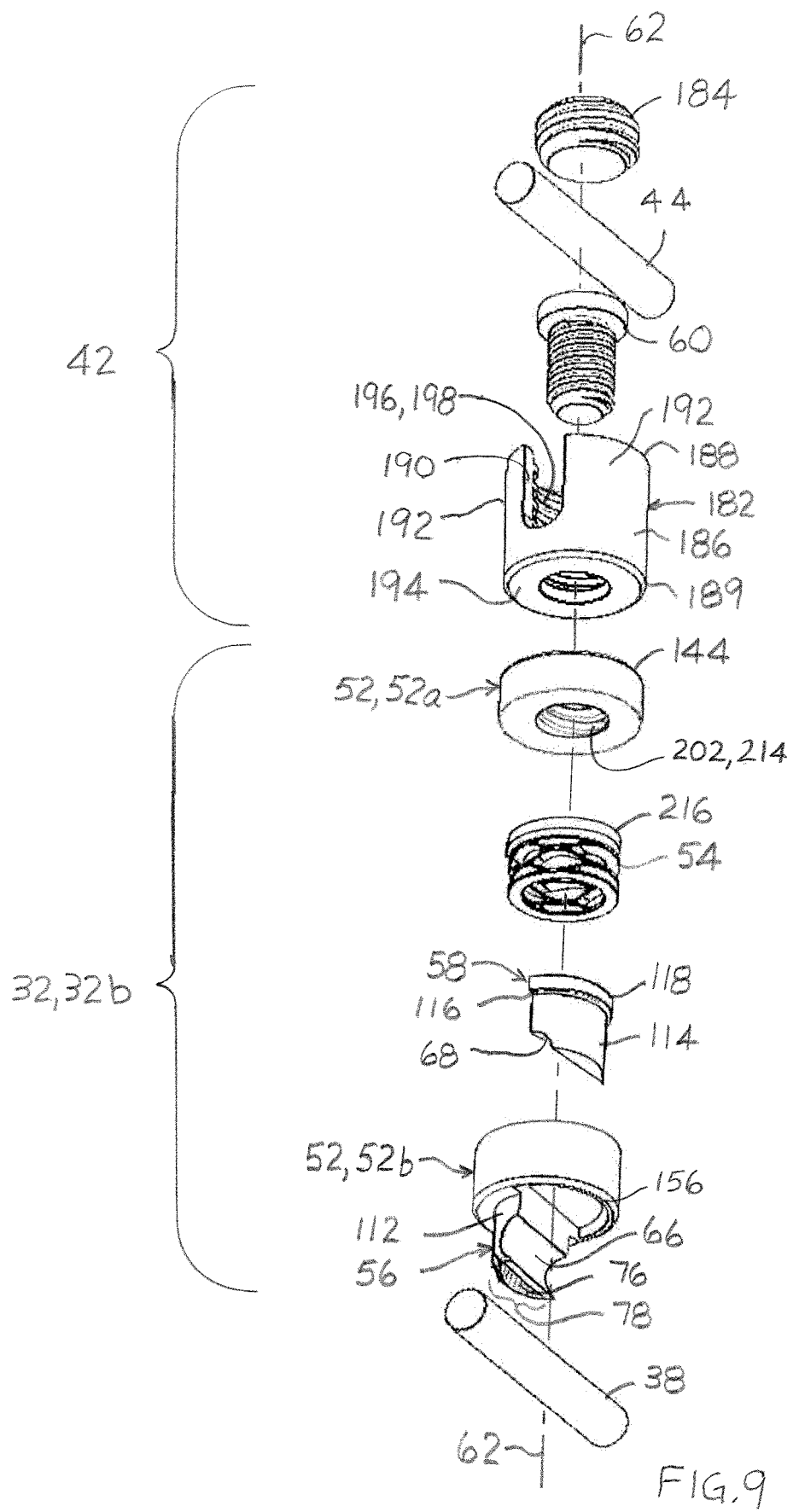
FIG. 9 is an exploded, lower perspective view of the clamp assembly and receptacle assembly of FIG. 8 according to an embodiment of the disclosure.

In the clamped configuration of FIGS. 5 and 6, the distal tangential extremities 74 and 84 define an angular gap 4 about the midpoint axis 70. In some embodiments, the angular gap 4 is in a range of 60 degrees to 165 degrees inclusive. In some embodiments, the angular gap 4 is in a range of 140 degrees to 70 degrees inclusive. In some embodiments, the angular gap 4 is in a range of 120 degrees to 80 degrees inclusive. Herein, a range that is said to be "inclusive" includes the end point values of the stated range as well as all values between the endpoint values.

In the depicted embodiment, the extension receptacle assembly 42 includes a rod receptacle 182, the fastener 60, and a set screw 184 for securing the extension spinal support rod 44 thereto. The rod receptacle 182 includes a side wall 186 having a proximal end 188 and a distal end 189 and defining a pair of diametrically opposed slots 190 that extend from the proximal end 188, with side wall segments 192 being separated by the opposed slots 190. The rod receptacle 182 may further include a flange portion 194 that extends radially inward from the distal end 189 of the side wall 186. The extension rod receptacle 182 may also include an interior surface 196 that includes threads 198 that surround the central axis 62 and are configured to threadably engage the set screw 184.

In assembly, the rod receptacle 182 is aligned with the clamp assembly 32*a* along the central axis 62, with the flange portion 194 at the distal end 189 of the rod receptacle 182 being adjacent the flange portion 146 at the proximal end 144 of the housing 52. The fastener 60 is inserted through the proximal end 188 of the rod receptacle 182 and through the flange portions 146 and 194 to engage the threads 124 of the clamping jaws 56 and 58. The fastener 60 is rotated to threadably engage the threads 124 and to draw the clamping jaws 56 and 58 toward the proximal end 144 of the housing 52 (upward in FIG. 6). This drawing action on the clamping jaws 56 and 58 further compresses the spring 54 to exert a greater force against the flange portions 118 of the clamping jaws 56 and 58, thereby securing the clamping jaws 56 and 58 to the base spinal support rod 38 in the clamped configuration. The drawing action also draws the tangential relief slots 126 further into the housing 52 and past the lock ring 65, so that the tangential relief slots 126 are not positioned to facilitate rotation of the clamping jaws 56 and 58. In this way, rotation of the clamping jaws 56 and 58 is disabled or substantially restricted when in the implanted configuration (FIG. 6). Furthermore, prior to tightening of the fastener 60, the rod receptacle 182 may be pivoted about the central axis 62 in any rotational orientation relative to the clamp assembly 32*a*. In the depicted embodiment, the extension spinal support rod 44 is inserted into the diametrically opposed slots 190 and the set screw 184 drawn tight to secure the extension spinal support rod 44 against either the distal ends of the opposed slots 190 (depicted) or against the top of the fastener 60.

The rod receptacle 182 may also be configured with external threads (not depicted) to accommodate a cap (not depicted) to prevent separation of the side wall segments 190 and the attendant slippage between the set screw 184 and the threads 198 of the rod receptacle 182. The external threads and cap arrangement is described in further detail at U.S. Provisional Patent Application No. 62/500,820 to Abbasi, filed May 3, 2017, and owned by the owner of the present application, the disclosure of which is incorporated by reference herein except for express definitions and patent claims contained therein. The rod receptacle 182 may also be configured to accommodate a double-threaded reinforcement cap (not depicted), as described at U.S. Provisional Patent Application No. 62/500,719 to Abbasi, filed May 3, 2017, and owned by the owner of the present application, the disclosure of which is incorporated by reference herein except for express definitions and patent claims contained therein.

Referring to FIG. 7, an example of the teeth 78, 92 is depicted according to an embodiment of the disclosure. In this non-limiting example, the teeth 78, 92 are a matrix of pyramidal projections, each projection having a base dimension and a height dimension that is within a range of 50 micrometers to 300 micrometers inclusive.

Referring to FIGS. 8 through 11, a clamp assembly 32*b* is depicted according to an embodiment of the disclosure. The clamp assembly 32*b* includes many of the same components and attributes as the clamp assembly 32*a*, which are indicated with same-numbered numerical references. The clamp assembly 32*b* includes a coupler 202 for mounting of the extension receptacle assembly 42. In some embodiments, an inner diameter 204 of the flange portion 146 at the proximal end 144 of the housing 52 is threaded to define a tapped hole 206. In such an embodiment, the coupler 202 is provided by the fastener 60 engaged with the tapped hole 206.

Figure 10:
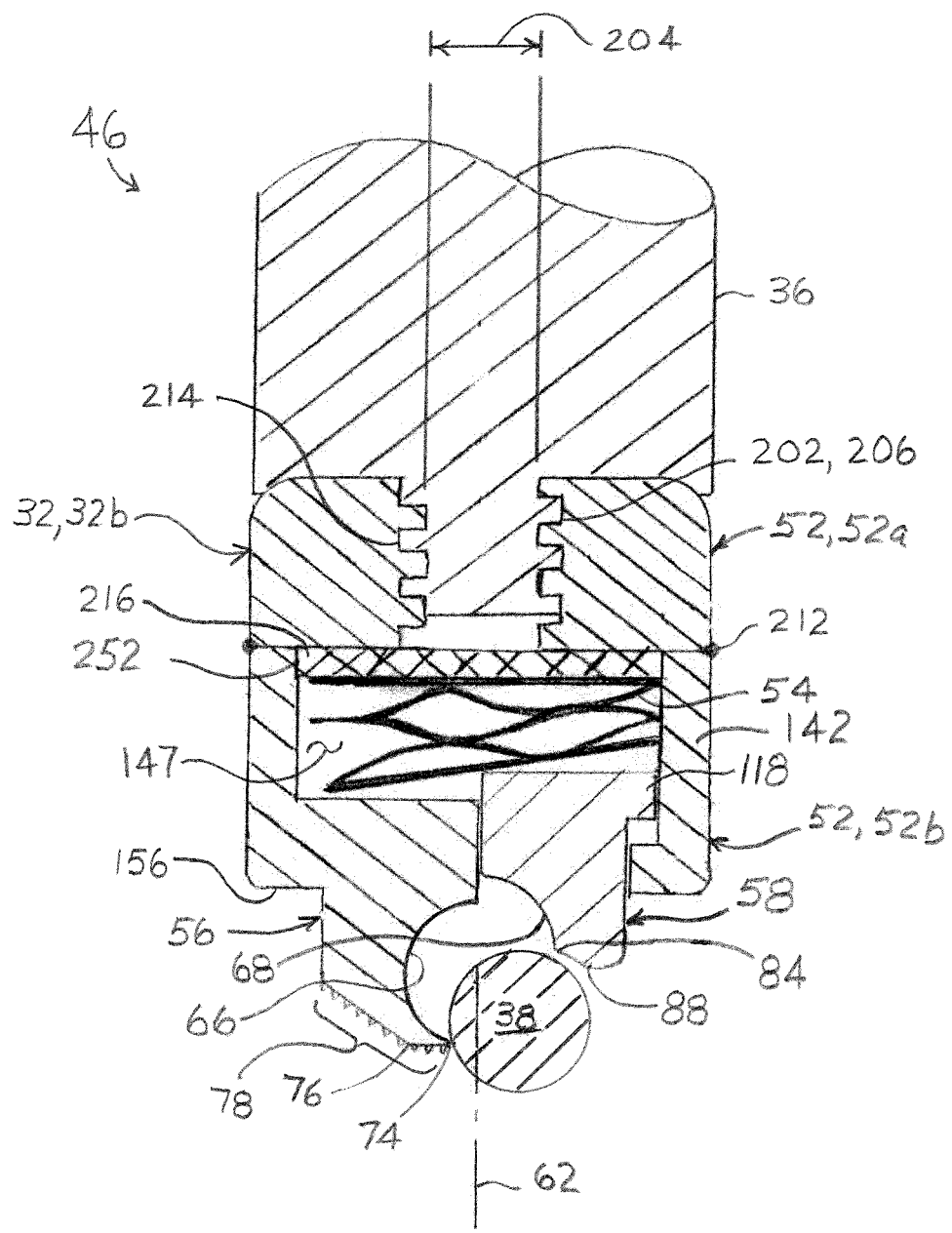
FIG. 10 is a partial sectional side view of the clamp assembly of FIG. 8 in a vibration configuration according to an embodiment of the disclosure.
Figure 11:
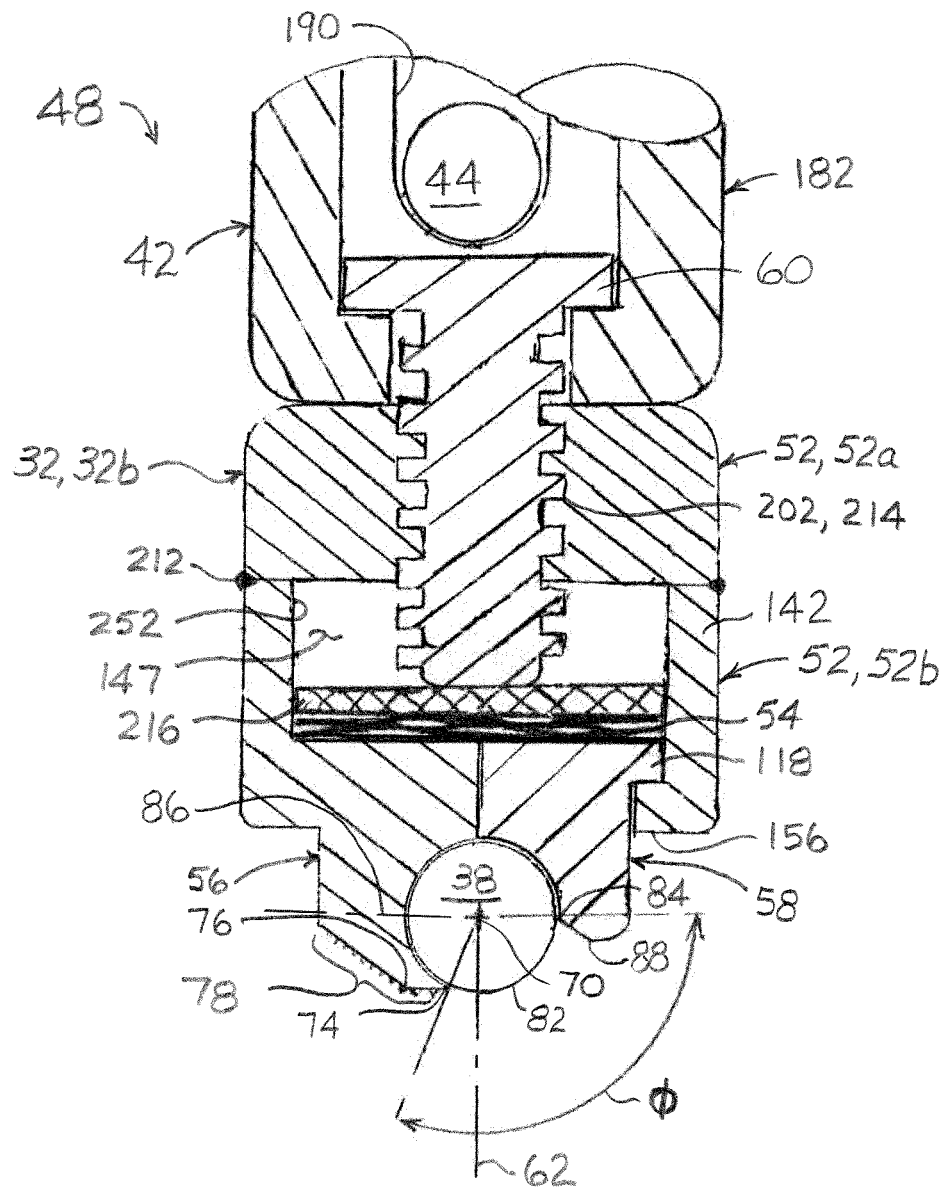
FIG. 11 is a partial sectional side view of the clamp assembly of FIG. 8 in an implanted configuration according to an embodiment of the disclosure.
Figure 12:
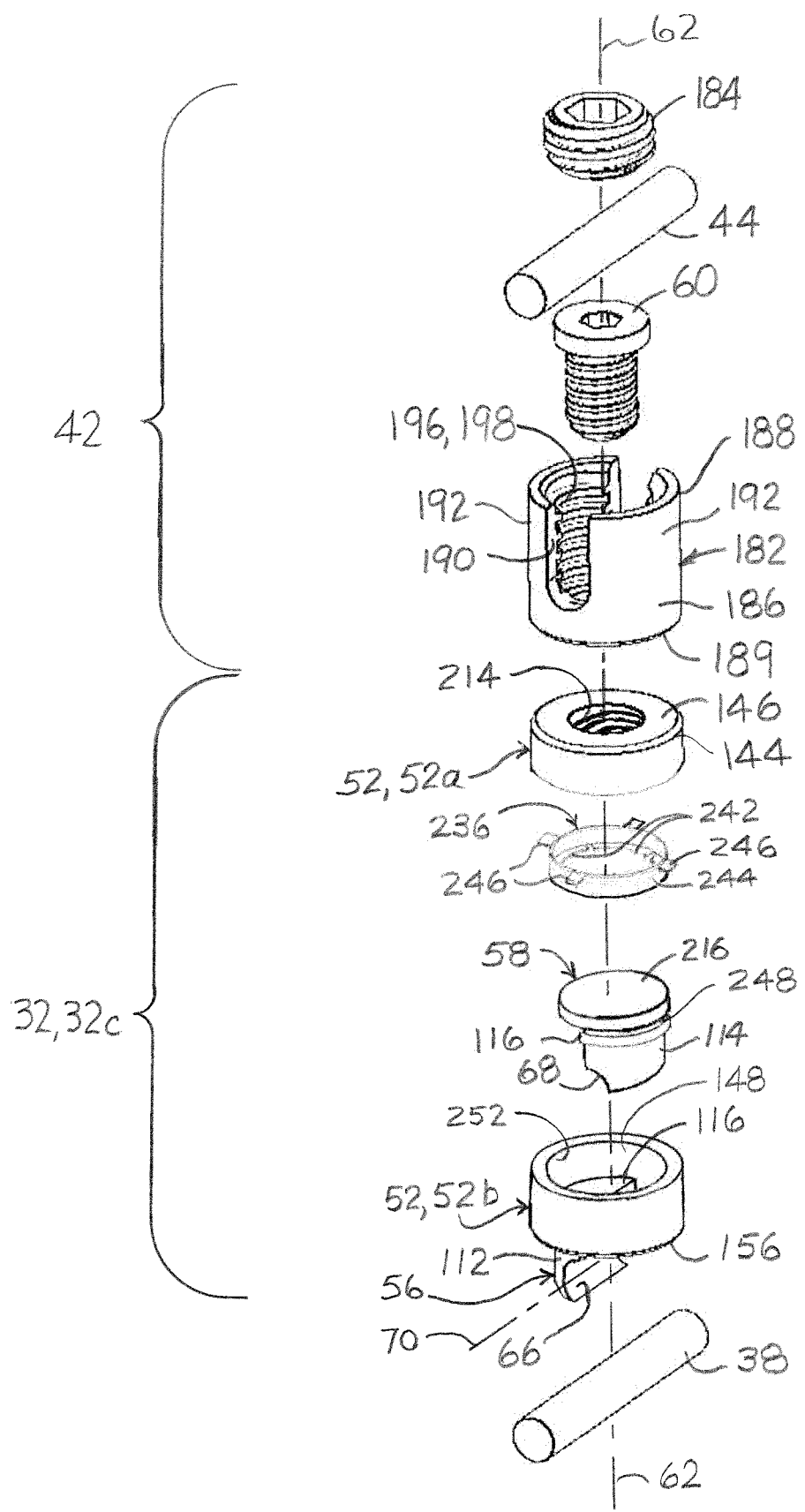
FIG. 12 is an exploded, upper perspective view of a clamp assembly having a fixed jaw and a translatable jaw with clip retention in combination with a receptacle assembly according to an embodiment of the disclosure.
Figure 13:
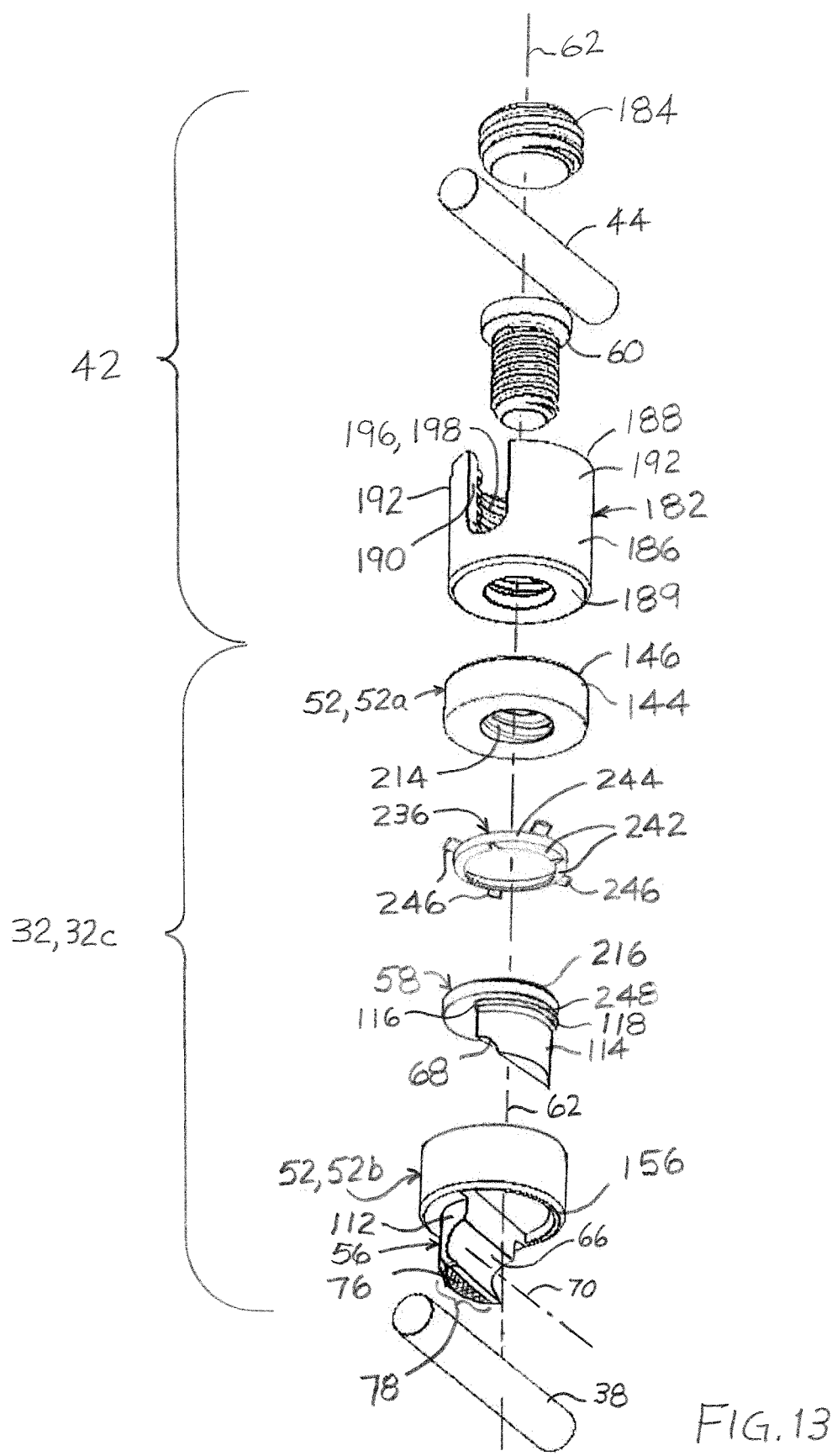
FIG. 13 is an exploded, lower perspective view of the clamp assembly and receptacle assembly of FIG. 12 according to an embodiment of the disclosure.

For the clamp assembly 32*b*, the housing 52 and the longer clamping jaw 56 are integral, for example by machining as a unitary component or by joining of separate pieces in a welding or brazing procedure for permanent connection. The housing 52 may be bifurcated into two components 52*a* and 52*b* to facilitate assembly. The housing components 52*a* and 52*b* may be joined, for example, by a weld 212 (depicted), brazing, or threaded engagement. Also, the shorter jaw 58 may be configured to rotate as depicted for the clamp assembly 32*a*, or to translate axially along or parallel to the central axis 62, as depicted in FIGS. 10 and 11.

In some embodiments, the clamp assembly 32 and the transmission line 36 are connected by the same coupler 202 that connects the clamp assembly 32 and extension receptacle assembly 42, for example a threaded connector 214 engaged with the tapped hole 206, as depicted for the clamp assembly 32*b*. The clamp assembly 32, 32*b* is used to cut through tissue that is proximate and adjacent the base spinal support rod 38 to clear it of tissue build up, as depicted in FIG. 10. Once the base spinal support rod 38 is sufficiently clear of tissue, the clamp assembly 32, 32*b* may be configured in the implanted configuration 48 and joined to the base spinal support rod 38 (FIG. 11). A blank flange 216 may be disposed between the fastener 60 and the spring 54 for compression of the spring 54 with the fastener 60. The blank flange 216 may be separate from or, alternatively, integral with the spring 54. In some embodiments, the fastener 60 is sized to completely or nearly completely compress the spring 54 to effect the clamping of the clamp assembly 32*b* to the base spinal support rod 38. Also, in some embodiments, the distal tangential extremity 74 of the longer clamping jaw 56 does not reach the central axis 62, and the longer clamping jaw 56 does not extend distal to the base spinal support rod 38.

Functionally, in the vibration configuration 46 (FIG. 10), having the housing 52 and the longer clamping jaw 56 integral facilitates transfer of ultrasonic vibration from the transmission line 36 to the teeth 78 for more efficient operation. The spring 54 biases the shorter clamping jaw 58 into the clamped position adjacent the longer clamping jaw 56. By sizing the fastener 60 to completely or nearly completely compress the spring 54 for the clamping, the shorter clamping jaw 58 is rigidly set in place on the base spinal support rod 38, without any appreciable give that could otherwise cause the shorter clamping jaw 58 to become dislodged. By configuring the distal tangential extremity 74 of the longer clamping jaw 56 to not reach the central axis 62, and not extending the longer clamping jaw 56 distal to the base spinal support rod 38, a low distal profile 218 is defined to reduce the amount of tissue that would otherwise have to be removed for implantation of the clamp assembly 32*b*.

Referring to FIGS. 12 through 15, a clamp assembly 32*c* is depicted according to an embodiment of the disclosure. The clamp assembly 32*c* includes many of the same components and attributes as the clamp assemblies 32*a* and 32*b*, which are indicated with same-numbered numerical references. As with the clamp assembly 32*b*, the housing 52 and the longer clamping jaw 56 are integral for the clamp assembly 32*c*, and the housing 52 may be bifurcated into two components 52a and 52b that may be joined, for example, by the weld 212 (depicted), brazing, or threaded engagement.

For the clamp assembly 32c, the blank flange 216 is integral with the shorter clamping jaw 58 at the proximal end 116. In some embodiments, a retention clip 236 is positioned adjacent the interior surface 148 of the interior chamber 147 of the housing 52. The retention clip 236 includes a lip portion or portions 242 that project radially inward, toward the central axis 62. The retention clip 236 may also include a ring portion 244 from which the lip portion(s) 242 depend. In some embodiments, the retention clip 236 is suspended by a projecting portions or portions 246 that are captured between the components 52a and 52b of the housing 52 (depicted). Alternatively, the retention clip 236 may be affixed to the interior surface 148 of the housing 52, for example by tac welding or brazing (not depicted).

The lip portion(s) 242 of the retention clip 236 are positioned to capture and secure the blank flange 216 at a proximal end 252 of the housing chamber 147. The shorter clamping jaw 58 may include a groove 248 at the base of the blank flange 216 to accommodate the lip portion(s) 242.

Figure 14:
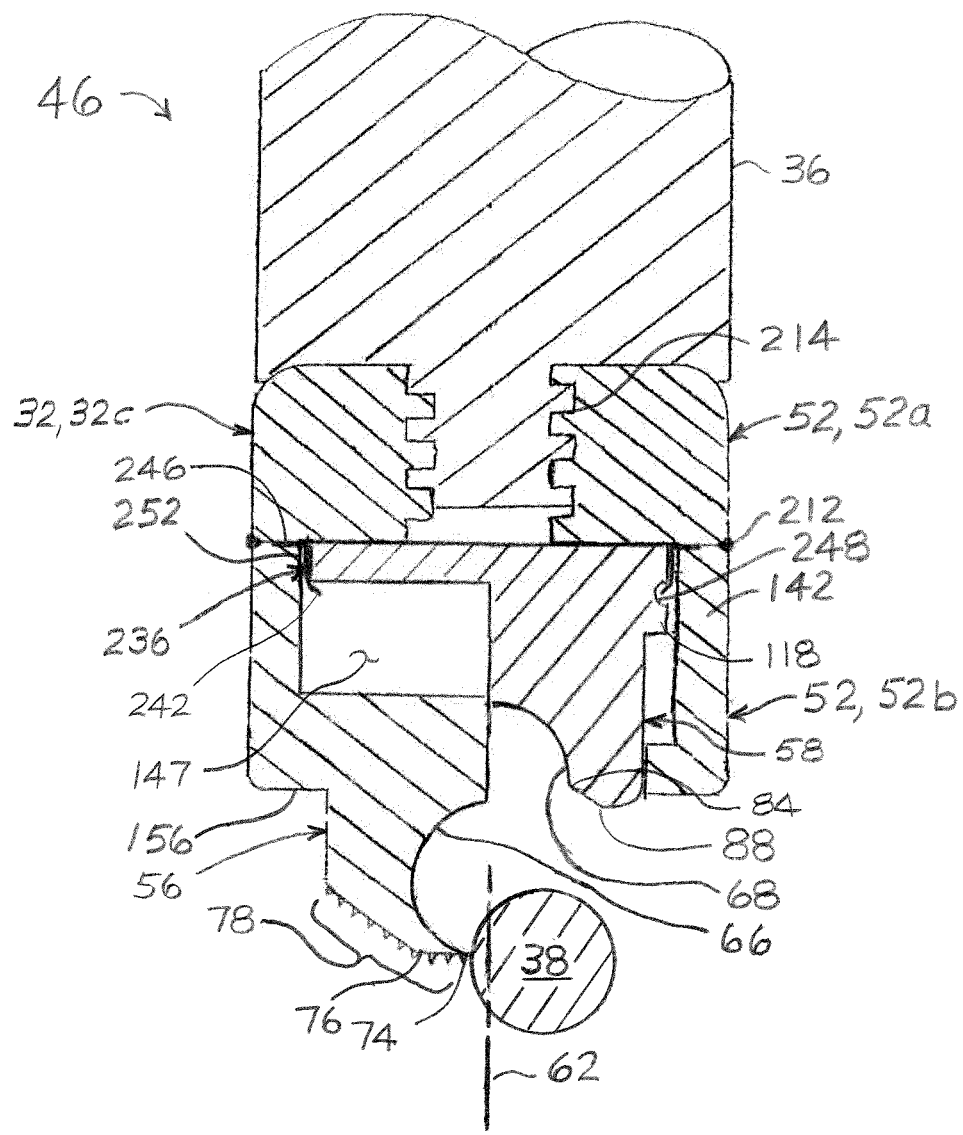
FIG. 14 is a partial sectional side view of the clamp assembly of FIG. 12 in a vibration configuration according to an embodiment of the disclosure.
Figure 15:
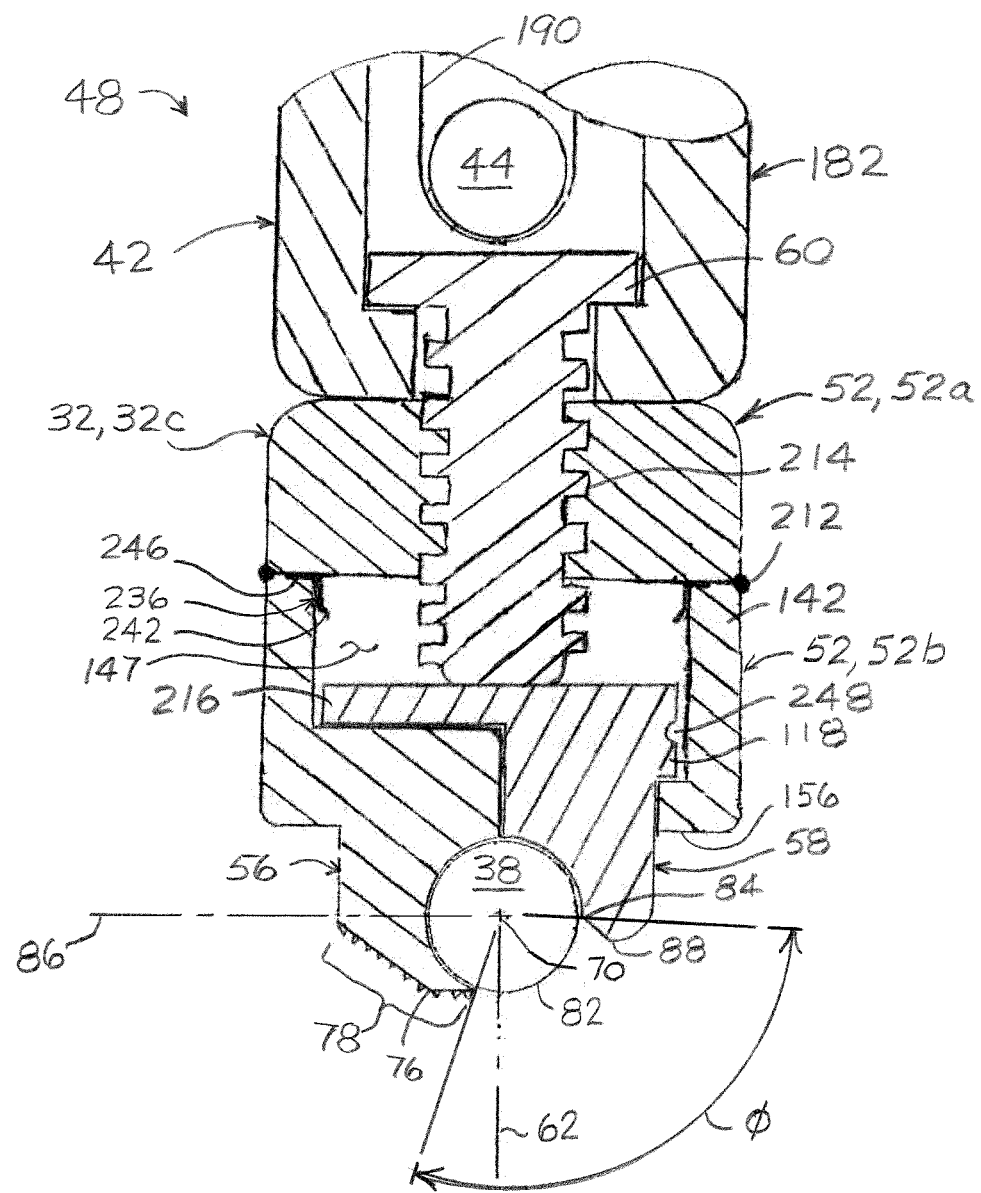
FIG. 15 is a partial sectional side view of the clamp assembly of FIG. 12 in an implanted configuration according to an embodiment of the disclosure.

Functionally, the retention clip 236 holds the shorter clamping jaw 58 in a retracted configuration when the clamp assembly 32c is in the vibration configuration 46 (FIG. 14). In the implanted configuration 48, the fastener 60 is threaded into the interior chamber 147 of the housing 52 and exerted against the blank flange 216. As threading of the fastener 60 into the housing 52 continues, the blank flange 216 is forced through the lip portion(s) 242 and dislodged from the retention clip 236, so that the shorter clamping jaw 58 is translated axially along or parallel to the central axis 62. The shorter clamping jaw 58 is thereby translated into position on the base spinal support rod 38. The fastener 60 is extended into the housing 52 and against the blank flange 216 to secure the shorter clamping jaw 58 against the base spinal support rod 38.

Referring to FIG. 16, a method 260 for tissue removal and subsequent mounting of the extension receptacle assembly 42 and clamp assembly 32 to the base spinal support rod 38 is depicted according to embodiments of the disclosure. In some embodiments, a kit 256 is provided for implementation of the method 260 (step 262). The kit 256 may include all of or certain components of the clamp assembly 32, all of or certain components of the receptacle assembly 42, and operating instructions 258 (FIG. 1).

In some embodiments, the operating instructions 258 include connecting the ultrasonic generator 34 to the coupler 202 of the clamp assembly 32 (step 264) and energizing the ultrasonic generator 34 to ultrasonically vibrate the clamp assembly 32 (step 266). Communication between the ultrasonic generator 34 and the clamp assembly 32 may be provided by the transmission line 36. The operating instructions 258 may also include cutting through built up tissue that is on and in the vicinity of the base spinal support rod 38 with the clamp assembly 32 after energizing the ultrasonic generator 34 (step 268). After cutting through and clearing the tissue from the base spinal support rod 38, the ultrasonic generator 34 may be de-energized and the clamp assembly 32 disconnected from the coupler 202 of the clamp assembly 32 (step 270). Other method steps may be inferred from descriptions of operation and implantation of the clamp assemblies 32 above (e.g., attend to FIGS. 2 through 6 for clam assembly 32a).

In some embodiments, the operating instructions 258 include coupling the rod receptacle 128 to the coupler 202 of the clamp assembly (step 272). The operating instructions 258 may include engaging the engagement surface 66 of the first jaw 56 of the clamp assembly 32 with the base spinal support rod 38 (step 274), and, with the engagement surface 66 of the first jaw 56 engaged with the base spinal support rod 38, translating the second jaw 58 of the clamp assembly 32 onto the base spinal support rod 36 (step 276). The operating instructions 258 may include rotating the rod receptacle 128 to a desired rotational orientation on the clamp assembly 32. The operating instructions 258 may include affixing the clamp assembly 32 to the base spinal support rod 38 (step 278) with the rod receptacle 128 mounted to the coupler 202 of the clamp assembly 32. The operating instructions 258 may include securing the clamping jaws 56 and 58 to the base spinal support rod 38, for example with the fastener 60.

The operating instructions 258 may be provided on a tangible, non-transitory medium. Non-limiting examples of a tangible, non-transitory medium include a paper document and computer-readable media including compact disc and magnetic storage devices (e.g., hard disk, flash drive, cartridge, floppy drive). The computer-readable media may be local or accessible over the internet. The instructions may be complete on a single medium, or divided among two or more media. For example, some instructions may be written on a paper document that instruct the user to access one or more of the steps of the method over the internet, the internet-accessible steps being stored on a computer-readable medium or media. The instructions may be in the form of written words, figures, and/or video presentations.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, uncombined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. An ultrasonically assisted clamping system, comprising:
   a clamp assembly including a first clamping jaw and a second clamping jaw configured for mounting to a base spinal support rod, wherein:
      said clamp assembly is configured for selective coupling to an ultrasonic generator when said ultrasonically assisted clamping system is in a vibration configuration; and
      said clamp assembly is configured for securing said clamp assembly to a base spinal support rod when said ultrasonically assisted clamping system is in an implanted configuration,
   wherein at least one of said first clamping jaw and said second clamping jaw is configured for cutting through tissue proximate said base spinal support rod.

2. The ultrasonically assisted clamping system of claim 1, wherein said first clamping jaw and said second clamping jaw extend in an axial direction parallel to a central axis of said clamp assembly, said first clamping jaw defining a first axial length in said axial direction, said second clamping jaw defining a second axial length in said axial direction, said first axial length being greater than said second axial length.

3. The ultrasonically assisted clamping system of claim 2, wherein:
   a first engagement surface of said first clamping jaw defines a first distal tangential extremity;
   a second engagement surface of said second clamping jaw defines a second distal tangential extremity;
   said first distal tangential extremity and said second distal tangential extremity define an angular gap therebetween when said clamp assembly is in said implanted configuration, said angular gap being defined from a midpoint axis defined by said first clamping jaw and said second clamping jaw; and
   said angular gap is in a range of 60 degrees to 165 degrees inclusive.

4. The ultrasonically assisted clamping system of claim 3, wherein said central axis of said clamp assembly passes through said angular gap when said clamp assembly is in said implanted configuration.

5. The ultrasonically assisted clamping system of claim 1, wherein at least said first clamping jaw includes a plurality of teeth at a distal end thereof for said cutting through tissue proximate said base spinal support rod.

6. The ultrasonically assisted clamping system of claim 5, wherein said plurality of teeth include a matrix of pyramidal projections.

7. The ultrasonically assisted clamping system of claim 6, wherein each pyramidal projection defines a base dimension and a height dimension, each of said base dimension and said height dimension being within a range of 50 micrometers to 300 micrometers inclusive.

8. The ultrasonically assisted clamping system of claim 1 comprising a housing, said first clamping jaw being one of unitary with, welded to, and soldered to said housing.

9. The ultrasonically assisted clamping system of claim 8, wherein said second clamping jaw is disposed in said housing and translatable parallel to said central axis.

10. The ultrasonically assisted clamping system of claim 1, wherein an extension receptacle assembly is coupled to a proximal end of said clamp assembly when said ultrasonically assisted clamping system is in said implanted configuration.

11. The ultrasonically assisted clamping system of claim 10, wherein said clamp assembly includes a coupler for selective connection of both of said extension receptacle assembly and said ultrasonic generator.

12. The ultrasonically assisted clamping system of claim 11, wherein said coupler is a threaded coupling.

13. The ultrasonically assisted clamping system of claim 1, comprising an ultrasonic generator.

* * * * *